(12) United States Patent
Nocon et al.

(10) Patent No.: US 10,591,446 B2
(45) Date of Patent: Mar. 17, 2020

(54) SEALING MOVING WITH PISTON IN A HIGH-PRESSURE PUMP

(71) Applicant: Agilent Technologies, Inc., Santa Clara, CA (US)

(72) Inventors: Blasius Nocon, Waldbronn (DE); Joachim-Richard Wagner, Ettlingen (DE); Karsten Lehradt, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 94 days.

(21) Appl. No.: 15/300,267

(22) PCT Filed: Mar. 31, 2014

(86) PCT No.: PCT/IB2014/060330
§ 371 (c)(1),
(2) Date: Sep. 28, 2016

(87) PCT Pub. No.: WO2015/150863
PCT Pub. Date: Oct. 8, 2015

(65) Prior Publication Data
US 2017/0138913 A1   May 18, 2017

(51) Int. Cl.
*G01N 30/32* (2006.01)
*F04B 9/00* (2006.01)
(Continued)

(52) U.S. Cl.
CPC ............... *G01N 30/32* (2013.01); *F04B 9/00* (2013.01); *F04B 9/02* (2013.01); *F04B 9/06* (2013.01);
(Continued)

(58) Field of Classification Search
CPC .. G01N 30/32; G01N 2030/326; F04B 53/16; F04B 53/164; F04B 53/143; F16J 1/008; F16J 1/04; F16J 1/06
See application file for complete search history.

(56) References Cited

U.S. PATENT DOCUMENTS 3,958,903 A * 5/1976 Capelli ................. F04B 7/0007
                                                          417/503
4,003,679 A   1/1977 McManigill
(Continued)

FOREIGN PATENT DOCUMENTS

CN    101065279 A    10/2007
CN    101900098 B    12/2010
(Continued)

OTHER PUBLICATIONS

International Search Report from related International Application No. PCT/IB2014/060330.

*Primary Examiner* — Paul M. West (57) ABSTRACT

A piston member for a high-pressure pump for pumping fluid in a sample separation apparatus, wherein the piston member comprises a piston configured for being mountable to reciprocate in a piston chamber for displacing fluid, and a sealing for sealing between the piston member and the piston chamber when the piston member is mounted in the piston chamber to reciprocate, wherein the sealing is mounted on the piston so as to reciprocate together with the piston.

19 Claims, 3 Drawing Sheets

(51) Int. Cl.
    *F04B 9/06*     (2006.01)
    *F04B 9/02*     (2006.01)
    *F04B 37/12*     (2006.01)
    *F04B 13/00*     (2006.01)
    *F04B 53/14*     (2006.01)
    *F04B 53/16*     (2006.01)
    *F16J 1/04*     (2006.01)
    *F16J 1/00*     (2006.01)
    *F16J 1/06*     (2006.01)

(52) U.S. Cl.
    CPC .............. *F04B 13/00* (2013.01); *F04B 37/12* (2013.01); *F04B 53/143* (2013.01); *F04B 53/16* (2013.01); *F04B 53/164* (2013.01); *F16J 1/008* (2013.01); *F16J 1/04* (2013.01); *F16J 1/06* (2013.01); *G01N 2030/326* (2013.01)

(56) References Cited

U.S. PATENT DOCUMENTS

| | | |
|---|---|---|
| 4,347,131 A | 8/1982 | Brownlee |
| 5,656,034 A | 8/1997 | Kochersperger et al. |
| 7,223,080 B2 * | 5/2007 | Duron ...................... F04B 5/02 417/53 |
| 2005/0091972 A1 * | 5/2005 | Redman ................ F15B 11/022 60/413 |
| 2014/0314600 A1 * | 10/2014 | Ding .................. B05B 11/3023 417/437 |

FOREIGN PATENT DOCUMENTS

| | | |
|---|---|---|
| CN | 101990639 A | 3/2011 |
| CN | 102374292 A | 3/2012 |
| CN | 103261054 A | 8/2013 |

* cited by examiner

SEALING MOVING WITH PISTON IN A
HIGH-PRESSURE PUMP

RELATED APPLICATIONS

This application is the national stage of International Application No. PCT/IB2014/060330, filed Mar. 31, 2014, titled "SEALING MOVING WITH PISTON IN A HIGH-PRESSURE PUMP", the entire contents of which are incorporated herein by reference.

BACKGROUND ART

The present invention relates to a piston member, to a pump head, to a high-pressure pump for pumping fluid, to a sample separation apparatus, and to a method of manufacturing a piston member for a high-pressure pump for pumping fluid in a sample separation apparatus.

In a sample separation device based on the principle of liquid chromatography, a fluidic sample to be separated is injected in a mobile phase (such as a solvent composition), wherein the mixture may be pumped through conduits and a column comprising a material (stationary phase) which is capable of separating different components of the fluidic sample. Such a material, so-called beads which may comprise silica gel, may be filled into a column tube which may be connected to other elements (like a sampling unit, a flow cell, containers including sample and/or buffers) by conduits.

For pumping the mobile phase to the sample separation device, a pump may be implemented in which a piston reciprocates within a pumping chamber to thereby displace the mobile phase. For injecting a fluidic sample into the mobile phase, another metering pump may be implemented in a sample injector of the sample separation device to thereby inject the fluidic sample into the mobile phase.

U.S. Pat. No. 4,036,232 discloses an aspiration unit which will afford a uniform suction level for aspirating fluids from body cavities. The unit is composed of a double piston member, a first head of which is in sealing engagement with a syringe barrel and the second head of which is oppositely disposed and is contained in a telescoping member which is also receivable in the syringe barrel. Upon movement of the telescoping member outwardly from the syringe barrel, a vacuum will be created in the telescoping member as well as in that portion of the barrel member between the first piston member and the nozzle which is closed from atmosphere by means of a valve member. Upon insertion of a flexible tube into a body cavity and opening of the valve member, fluid will be aspirated into the syringe barrel by means of the partial vacuum created in the syringe barrel and in the telescoping member. A clamp means is provided to hold the telescoping member in the vacuum creating condition while the tubular member is inserted into a body cavity. The aspirating device is operable with one hand and is disposable.

U.S. Pat. No. 4,939,943 discloses a sample injector for a liquid chromatograph which comprises a high pressure syringe unit, a sample intake unit having a needle which can be introduced into a sample container as well as a seat, and a 6/2-way valve. The high pressure syringe unit is designed as a piston pump with a pump head and a piston which is driven by a motor via a drive mechanism. Pressurized liquid from a solvent delivery system can enter the pump head through an inlet port and flow along the piston to an outlet port. When sample is to be injected into a chromatographic column, the 6/2-way valve is first switched into the position depicted by dotted lines, the needle is introduced into the container and the piston is retracted by a corresponding distance. Thereafter, the valve is switched back to its original position so that solvent delivered from the solvent delivery system can transport the sample to the column. Since the solvent flushes the entire syringe unit, it is ensured that no sample residues remain in the syringe unit which would otherwise impair the chromatographic measuring process.

U.S. Pat. No. 6,984,222 discloses a plunger system for use in an injector-actuated syringe which includes a dynamic wedge seal which improves the sealing engagement between the plunger cover and syringe barrel, and flexible capture members extending from the rear surface of the plunger which permit the engagement and disengagement of the plunger from the injector drive means at any plunger position within the syringe. Further, the plunger systems include a contrast saving tip which expels the injection liquid from the syringe tip.

However, when the pressure values according to which fluid is pumped by the pump become larger and larger, a mechanically stable pump is required which is at the same time reliably sealed.

DISCLOSURE

It is an object of the invention to provide a pump being reliably sealed even at very high pressure values.

According to an exemplary embodiment of the present invention, a piston member for a high-pressure pump for pumping fluid (such as a liquid and/or a gas, optionally comprising solid particles) in a sample separation apparatus is provided, wherein the piston member comprises a piston configured for being mountable to reciprocate in a piston chamber for displacing fluid, and a sealing for sealing between the piston member and the piston chamber when the piston member is mounted in the piston chamber to reciprocate, wherein the sealing is mounted on the piston so as to reciprocate together with the piston.

According to another exemplary embodiment, a pump head for a high-pressure pump for pumping fluid in a sample separation apparatus is provided, wherein the pump head comprises a piston chamber delimiting a working volume, and a piston member having the above-mentioned features and mounted or mountable in the working volume of the piston chamber so that the sealing seals between the piston member and the piston chamber.

According to still another exemplary embodiment, a high-pressure pump for a sample separation apparatus is provided, wherein the pump comprises a piston member having the above-mentioned features.

According to still another exemplary embodiment, a sample separation apparatus for separating a fluidic sample in a mobile phase into a plurality of fractions is provided, wherein the apparatus comprises a high-pressure pump having the above-mentioned features and configured for driving a fluid comprising at least one of the mobile phase and the fluidic sample, and a separation unit configured for separating the fluidic sample into the plurality of fractions.

According to still another exemplary embodiment, a method of manufacturing a piston member for a high-pressure pump for pumping fluid in a sample separation apparatus is provided, wherein the method comprises providing a piston configured for being mountable to reciprocate in a piston chamber for displacing fluid, and rigidly mounting a sealing on the piston for reciprocating together with the piston and for sealing between the piston member and the piston chamber when the piston member is mounted in the piston chamber to reciprocate.

According to an exemplary embodiment, the piston and the sealing are rigidly connected to one another so as to be capable to move together during the reciprocation motion of the piston for displacing fluid in the piston chamber. By forming the piston and the sealing as one common member reciprocating together, the guidance of the piston in the piston chamber is significantly improved. With the improved guiding of the piston, an undesired abutment of the piston to the wall of the piston chamber may be advantageously avoided. This results from the fact that also the sealing securely connected to the piston contributes to the correct alignment and positioning of the piston within the piston chamber. Furthermore, the rigid connection between the piston and the sealing forms the basis for a significant reduction of the dead volume of fluid in the piston chamber, since this allows the sealing to be located in a front region within the piston chamber, i.e. closer to a front flange face of the piston chamber delimiting the working chamber.

In the following, further embodiments of the piston member, the pump head, the high-pressure pump, the sample separation apparatus, and the method will be explained.

In an embodiment, the sealing is arranged at or mounted on a front end of the piston, in particular on a flange face of the piston and/or located around a lateral surface of the piston next to the flange face. The front end hereby corresponds to a free end of the piston. The front end may be movable almost up to a flange face of the piston chamber and opposes a back end of the piston which may be mounted on a piston foot and/or which is located closer to a piston actuator driven by a drive unit than the front end. When the sealing is arranged at the end of the piston displacing the fluid, the dead volume of fluid in the piston chamber can be rendered extremely small, and significantly smaller as compared to a conventional approach in which the sealing is fixedly arranged at the piston chamber while the piston reciprocates relative to the sealing. Thus, problems with carryover of mobile phase and/or sample among different analysis procedures can be significantly reduced by the fixed assembly of the sealing in a front portion of the piston.

In an embodiment, the sealing is arranged at the front end of the piston so as to constitute the entire flange face of the piston member (wherein optionally a portion of the sealing may be located around a lateral surface of the piston next to the flange face). In such an embodiment, the sealing may alone displace the fluid or may at least significantly contribute to this displacement. Therefore, the effective area of the piston member acting on the fluid is advantageously high.

In an embodiment, the sealing comprises or consists of an elastic material, in particular a (particularly soft) plastic material. By configuring the sealing from a resilient material, it is possible that the sealing fills even small gaps between the piston-sealing-assembly/piston member on the one hand and the wall of the piston chamber on the other hand, thereby promoting the sealing performance and reducing the dead volume of fluid in the piston chamber. For instance, the sealing may be made of a rubber or soft plastic material.

In an embodiment, the sealing is made of a chemically inert material (such as Polytetrafluoroethylene (PTFE) or a Polyethylene (PE) based plastic), in particularly of a solvent inert material. This material selection ensures that the sealing is not deteriorated or damaged by chemically aggressive fluid displaced under contribution of the sealing. For instance, for liquid chromatography applications, aggressive solvent materials such as organic solvent-like methanol or acetonitrile may be used and may be tolerated by the chemically inert sealing without deteriorating the sealing. In an embodiment, the sealing may be also made of a biologically inert or bioinert material, so as to render the piston member capable of withstanding, without deterioration, the presence of a biologic fluidic sample which may be displaced by the piston with integrated sealing.

In an embodiment, the piston comprises or consists of a rigid material, in particular one of the group consisting of a metal and a ceramic. Such materials are robust enough to withstand the high mechanical loads acting on the piston upon displacing fluids even at high-pressure values of several hundred bar or more.

In an embodiment, the sealing is mounted on the piston by at least one of the group consisting of a form closure (i.e. by mating inverse shapes of piston and sealing, so as to securely fix the sealing on the piston by a press-fit or a clamping force or by shrinking) and a material bond (in particular an adhesive bond, i.e. by gluing the sealing to the piston). For example, the shape of the sealing at a piston connection section may match and may be inverse to a shape of the piston at a front section so that both components can be connected to one another without the danger of an undesired separation under mechanical loads. The secure connection of sealing and piston may be ensured or enhanced by the adhesion of the sealing to the piston.

However, in a preferred embodiment, the sealing is fastened at the piston in a purely mechanical way. This avoids to introduce adhesive material or the like in the piston chamber which eliminates any risk that aggressive solvent decomposes the adhesive and pollutes pumped mobile phase or fluidic sample.

In an embodiment, the sealing comprises at its front face an annular recess delimiting a central protrusion with regard to an exterior sealing lip. In such an embodiment, the circumferential sealing lip abutting along its entire perimeter with compressive force against the wall of the piston chamber may serve as the actual sealing element closing any gap between piston chamber and piston. The provision of the central protrusion may work against the fluid to be displaced and ensures a small dead volume. The central protrusion may hence advance within the piston chamber up to an end position and may contribute significantly to the fluid displacement. The annular recess or ring groove may serve as a mounting base or accommodation volume for mounting an additional member (such as a spring as a biasing element, see following description).

In an embodiment, the piston member further comprises a biasing member, in particular a spring member (such as a flat spring), arranged at the sealing for promoting the sealing performance by an elastic force, in particular a spring force. The provision of a spring or another biasing member can improve the sealing performance, for instance by imparting an outwardly oriented biasing force from the piston member onto a circumferential wall surface of the piston chamber.

In an embodiment, the biasing member is arranged within the annular recess or pocket. This results in a very compact piston member simultaneously providing a highly reliable sealing function. Hence, a sealing with integrated sealing force enhancing biasing member moving along with the piston may be provided. However, in an alternative embodiment, it is also possible that the spring is arranged at another location, for example between the piston and the sealing.

In an embodiment, the piston member is mounted in the piston chamber so that the piston member is forwardable up to its front end position in the piston chamber which is located less than approximately 0.5 mm, particularly less than approximately 0.3 mm, from a flange face of the piston chamber delimiting the working volume. By taking this measure, an extremely small dead volume within the piston chamber may be achieved. When the elastic sealing constitutes the front end of the piston member, the latter may be advanced almost up to the flange face of the piston chamber because the elasticity of the sealing provides a protection against an undesired hard hitting of the piston member against the front wall of the working chamber. This further reduces the dead volume of the pump.

In an embodiment, the piston chamber comprises a hollow cylinder (for instance of ceramic material) laterally delimiting the working chamber and a surrounding pump head body which also defines the flange face of the piston chamber. A flat sealing (for instance gold-plated) may be arranged between the hollow cylinder and the pump head body for sealing a gap in between.

In an embodiment, the piston member comprises (apart from the sealing) a piston assembly constituted by the piston and a piston base (or piston foot) at which the piston is (detachably or fixedly) mounted, wherein the piston forms a free front section of the piston assembly displacing the fluid and the piston base forms a rear section of the piston assembly lockable to a piston actuator (which, in turn, is driven by a drive unit to drive, in turn, the piston member). The piston may be a cylindrical member having a front face actually displacing the fluid in collaboration with the sealing, and having a lateral surface sliding along the working chamber. The piston base or piston foot comprises a recess or accommodation volume for accommodating an end of the piston and comprises another section cooperating with a piston actuator supplying driving energy to the piston assembly.

In an embodiment, the pump head comprises a movable piston guide unit arranged on the piston member and extending into the working volume when the pump displaces fluid. The provision of such a guide member moving with the piston may further improve the accuracy according to which the piston-sealing-assembly/piston member reciprocates within the working chamber. Thus, inaccuracies concerning the displaced fluid in terms of flow rate or volume can be efficiently suppressed. The piston guide unit may be located axially behind (i.e. further away from the flange face of the piston chamber) the sealing to thereby keep the dead volume small. In an embodiment, the movable piston guide unit is a sleeve which forms part of the piston assembly and guides the piston assembly at the piston, i.e. at a front position.

In an embodiment, the pump head comprises a static piston guide unit arranged at the piston chamber (for instance shaped as a sleeve). The static piston guide unit may be positioned at a larger distance to a flange face of the piston chamber compared to the static piston guide unit. The provision of a static piston guide, wherein both piston guide units may be spaced relative to one another along the reciprocation direction of the piston-sealing-assembly, provides an additional contribution to the extremely accurate fluid displacement in the pump chamber. When the piston member comprises the piston and an additional piston foot on which the piston is mounted, the movable piston guide unit may be located on the piston and the static piston guide unit may be located on the pump chamber and may operate on the piston foot. In an embodiment, the static piston guide unit is a sleeve which forms part of the piston chamber and guides the piston assembly at the piston base, i.e. at a rear position.

In an embodiment, the pump comprises a pump head which comprises the piston member having the above mentioned features. Moreover, the pump may comprise a pump base to be assembled with the pump head and comprising a piston drive configured for driving the piston to reciprocate within the piston chamber in an assembled state. After wear out of the piston member, the pump head may be disassembled from the pump base and may be assembled again with a replaced piston member of pump head.

In an embodiment, the pump comprises a back-driving mechanism, in particular a back-driving spring, arranged to provide a back-driving force to the piston after having forwarded the piston to its upper end position in the piston chamber by the piston drive. When the piston sealing assembly advances or moves forwardly in the piston chamber, the back-driving mechanism embodied as a helical spring arranged around the piston chamber may be biased, so that, when the piston sealing assembly has reached the front end in the piston chamber, the biased spring may relax to thereby automatically back-drive the piston sealing assembly to a rear position. Such a back-driving mechanism reduces the energy required for operating the high-pressure pump.

In an embodiment, the pump is configured as a metering device for a sample injector of the sample separation apparatus configured for metering the fluidic sample to be separated into fractions. Such a metering pump may be present in a sample injector of a liquid chromatography device. For instance, a needle of the sample injector may dip into a vial comprising sample fluid, and the metering device may be operated to draw in sample in a sample loop between needle and metering device. Subsequently, after the needle has been driven back into a seat of the sample injector, the metering pump may move forwardly so as to press the sample fluid from the sample loop and optionally a fluidic valve into a flow path or main path between another high-pressure pump and a separation unit such as a chromatography column. In such a metering pump, the accurate displacement of fluid is of utmost importance, as well as a small dead volume provided by the high-pressure pump according to an embodiment of the invention.

In another embodiment, the pump is configured as a mobile phase drive configured for driving a mobile phase towards a separation unit of a sample separation apparatus. Thus, also the previously mentioned high-pressure pump pumping mobile phase to the separation unit and also pumping fluidic sample injected via the sample injector into the flow path or main path may be equipped with a pump according to an exemplary embodiment of the invention. Such a pump operates under extremely high-pressure conditions so that the accurate displacement of fluid and the robust configuration of the piston member is advantageously implementable here.

Pumps according to various embodiments may be implemented for very different applications such as analytic pumps, flush pumps, etc.

In an embodiment, the pump comprises a fluid inlet interface configured for providing a fluid communication between fluid to be pumped and the working volume. Such a fluid inlet interface may be configured for supplying fluid to be pumped by the pump into the piston chamber. In an embodiment, the pump further comprises a fluid outlet interface for outletting fluid pumped by the pump and configured for providing a fluid communication with the working chamber. Such a fluid outlet interface may, like the fluid inlet interface, be configured as a valve, wherein the pumped fluid can be removed from the pumping chamber to a connected fluidic member via the fluid outlet interface.

In an embodiment, the pump is configured for pumping the fluid with a pressure of at least 500 bar, in particular at least 1000 bar, more particularly at least 1500 bar. In the presence of such high pressure values, the highly reliable sealing performance, the precise piston guidance and the small dead volume as achievable by exemplary embodiments are particularly pronounced.

The separation unit may be filled with a separating material. Such a separating material which may also be denoted as a stationary phase may be any material which allows an adjustable degree of interaction with a sample fluid so as to be capable of separating different components of such a sample fluid. The separating material may be a liquid chromatography column filling material or packing material comprising at least one of the group consisting of polystyrene, zeolite, polyvinylalcohol, polytetrafluoroethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the separation unit may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The separation unit may be a chromatographic column for separating components of the fluidic sample. Therefore, exemplary embodiments may be particularly implemented in the context of a liquid chromatography apparatus.

The fluid separation apparatus may be configured to conduct a liquid mobile phase through the separation unit. As an alternative to a liquid mobile phase, a gaseous mobile phase or a mobile phase including solid particles may be processed using the fluid separation apparatus. Also materials being mixtures of different phases (solid, liquid, gaseous) may be processed using exemplary embodiments. The fluid separation apparatus may be configured to conduct the mobile phase through the system with a high pressure, particularly of at least 600 bar, more particularly of at least 1200 bar.

The fluid separation apparatus may be configured as a microfluidic device. The term "microfluidic device" may particularly denote a fluid separation apparatus as described herein which allows to convey fluid through microchannels having a dimension in the order of magnitude of less than 500 µm, particularly less than 200 µm, more particularly less than 100 µm or less than 50 µm or less.

Exemplary embodiments may be implemented in a sample injector of a liquid chromatography apparatus which sample injector may take up a sample fluid from a fluid container and may inject such a sample fluid in a conduit for supply to a separation column. During this procedure, the sample fluid may be compressed from, for instance, normal pressure to a higher pressure of, for instance several hundred bars or even 1000 bar and more. An autosampler may automatically inject a sample fluid from the vial into a sample loop (alternatively, a fixed loop concept may be applied). A tip or needle of the autosampler may dip into a fluid container, may suck fluid into the capillary and may then drive back into a seat to then, for instance via a switchable fluidic valve, inject the sample fluid towards a sample separation section of the liquid chromatography apparatus.

The fluid separation apparatus may be configured to analyze at least one physical, chemical and/or biological parameter of at least one component of the sample fluid/fluidic sample in the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluid separation apparatus may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluid separation apparatus may be a High Performance Liquid Chromatography (HPLC) device by which different fractions of an analyte may be separated, examined and analyzed.

An embodiment of the present invention comprises a fluid separation apparatus configured for separating compounds of a sample fluid in a mobile phase. The fluid separation apparatus may comprise a mobile phase drive, such as a pumping system, configured to drive the mobile phase through the fluid separation apparatus. A separation unit, which can be a chromatographic column, is provided for separating compounds of the sample fluid in the mobile phase. The fluid separation apparatus may further comprise a sample injector configured to introduce the sample fluid into the mobile phase, a detector configured to detect separated compounds of the sample fluid, a collector configured to collect separated compounds of the sample fluid, a data processing unit configured to process data received from the fluid separation apparatus, and/or a degassing apparatus for degassing the mobile phase.

Embodiments of the present invention might be embodied based on most conventionally available HPLC systems, such as the Agilent 1290 Series Infinity system, Agilent 1200 Series Rapid Resolution LC system, or the Agilent 1100 HPLC series (all provided by the applicant Agilent Technologies—see www.agilent.com—which shall be incorporated herein by reference).

One embodiment comprises a pump having a piston for reciprocation in a pump working chamber to compress liquid in the pump working chamber to a high pressure at which compressibility of the liquid becomes noticeable. One embodiment comprises two pumps coupled either in a serial or parallel manner.

The mobile phase (or eluent) can be either a pure solvent or a mixture of different solvents. It can be chosen e.g. to minimize the retention of the compounds of interest and/or the amount of mobile phase to run the chromatography. The mobile phase can also be chosen so that the different compounds can be separated effectively. The mobile phase might comprise an organic solvent like e.g. methanol or acetonitrile, often diluted with water. For gradient operation water and organic are delivered in separate bottles, from which the gradient pump delivers a programmed blend to the system. Other commonly used solvents may be isopropanol, tetrahydrofuran hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The fluid is preferably a liquid but may also be or comprise a gas and/or a supercritical fluid (as e.g. used in supercritical fluid chromatography—SFC).

The pressure in the mobile phase might range from 2-200 MPa (20 to 2000 bar), in particular 10-150 MPa (100 to 1500 bar), and more particularly 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

The illustration in the drawing is schematic.

Before, referring to the drawings, exemplary embodiments will be described in further detail, some basic considerations will be summarized based on which exemplary embodiments of the invention have been developed.

In an embodiment, an analytic/flush pump head with a flange-sided piston sealing is provided.

In conventional approaches, a piston may be pushed through a fixed sealing into a volume delimited by a piston chamber, wherein fluid in this volume is then displaced. Such a concept has however the disadvantage of a large dead volume of for instance 60 µl in case of a 100 µl pump head. Thus, an entire fluid volume of 160 µl is required in this example. Caused by the relatively large dead volume, influences such as thermal expansion and compressibility of a solvent become pronounced. As a result of the large geometry/volume and the resulting high dead volume, the flush behavior (when changing solvent) is deteriorated, and system venting becomes difficult. As a result of the small distance between piston and pump chamber, a portion of laminar flow makes the mixing of solvent difficult. A conventional piston guidance may not be sufficient to safely prevent an undesired abutment of the piston against a side wall of the pump chamber in the presence of lateral forces.

Such an undesired collision or abutment may result in undesired abrasion of material from the piston chamber. Abrased material may consequently also be transported in an undesired way into an analytical system. Furthermore, when the piston abuts against a side wall of the piston chamber, it is possible that surface layers (such as chromium/nickel layers) of the piston chamber are deteriorated which causes damage of the piston chamber. For instance, this may result in an undesired corrosion.

In order to at least partially overcome the above-mentioned shortcomings by exemplary embodiments of the invention, the dead volume can be reduced and an undesired abutment of the piston at the piston chamber may be rendered unlikely or even impossible by the provision of a commonly moving piston-sealing-assembly constituted by a piston member according to an exemplary embodiment of the invention.

Reducing the dead volume may be achieved by the location of the sealing on the flange face of the piston, which may render it appropriate to adapt the material pairing between piston chamber and sealing. For instance, the piston chamber may be at least partially made of a ceramic material. Such a concept makes it possible to significantly reduce the dead volume (for instance to about 10% of the original value, for example from 60 µl to 6 µl). The smaller dead volume also significantly improves the behavior in terms of thermal expansion and solvent compressibility. The flush behavior as well as a venting of the system become significantly simpler and faster. Furthermore, a mixing performance in the working volume may be significantly improved by a fast turbulent flow in the relatively large mixing chamber.

According to an exemplary embodiment of the invention, an undesired abutment of the piston at the piston chamber may be safely prevented by the manufacture of the piston in one setting (for instance in one chucking) so that only minimal concentric deviations occur. Furthermore, this may be promoted by the manufacture of the piston chamber (which may be made of a ceramic cylinder and a carrier) in one setting (for instance in one chucking), resulting in only minimal concentric deviations of the entire piston chamber assembly. A static piston guide unit in the rear portion of the piston chamber may be provided with an extensive axial length, thereby rendering an abutment of the piston against the piston chamber even more unlikely. This can be further improved by the provision of a further separate movable piston guide unit on the piston directly behind the sealing, for instance embodied as a slitted plastic socket. In case of an undesired abutment of the piston, the resulting abrased material is not located directly in the analytical path but behind the sealing. A seal effect between the ceramic piston chamber and a pump head body can be provided or promoted by a gold-plated flat sealing.

Concluding, exemplary embodiments of the invention have the advantage that the dead volume is significantly reduced, that thermal expansion and compressibility of the solvent have only a small impact, that the tolerances are reduced in sum, that the piston can be guided extremely accurately, that the probability of an abutment of the piston on the piston chamber is reduced, that the robustness is improved by the elimination of a sealing surface, and that the mixing performance of the solvent is further improved.

Figure 1:
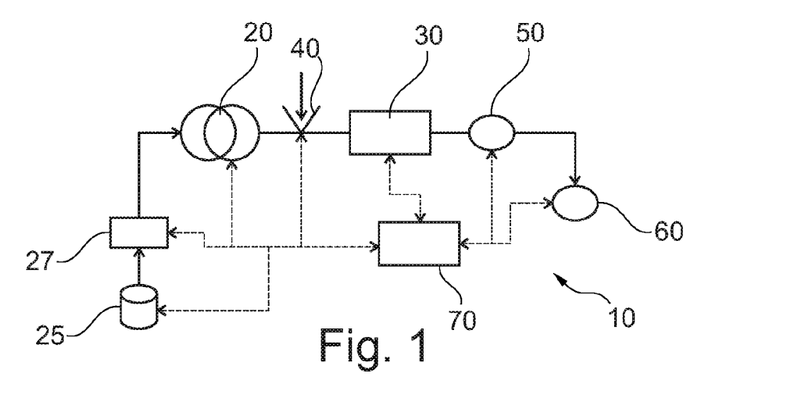
FIG. 1 shows a liquid separation device in accordance with embodiments of the present invention, particularly used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degasses and thus reduces the amount of dissolved gases in the mobile phase.

The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send in return information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

The pump 20 is configured for pumping the fluid with a pressure of at least 500 bar, in particular at least 1000 bar, more particularly at least 1500 bar.

Figure 2:
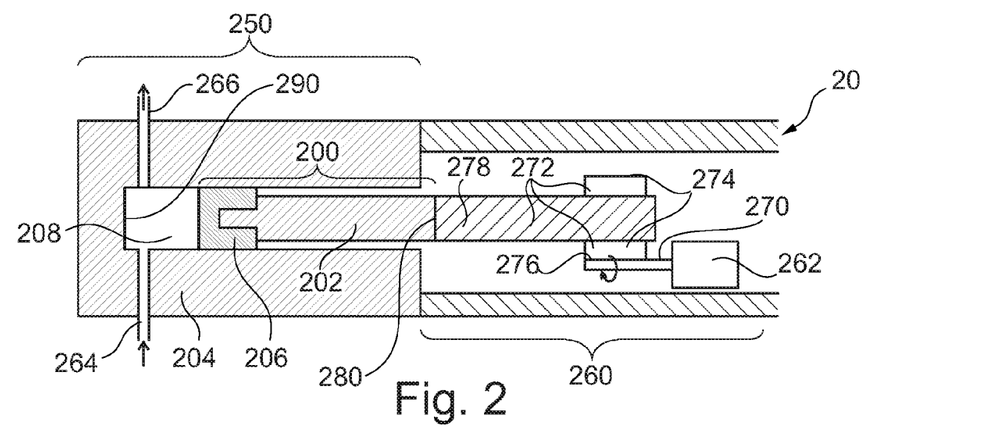
FIG. 2 illustrates a cross-sectional view of a pump according to an exemplary embodiment of the invention.

FIG. 2 shows a schematic cross-sectional view of a high-pressure pump 20 for a sample separation apparatus 10 as the one shown in FIG. 1 according to an exemplary embodiment of the invention.

The high-pressure pump 20 comprises a pump head 250 and a pump base 260 which is to be assembled with the pump head 250 and is actually assembled in the illustration of FIG. 2. The pump base 260 comprises a piston drive 262, such as an electric motor, which is configured for driving the piston 202 to reciprocate (along a horizontal direction according to FIG. 2, forwardly and backwardly) within piston chamber 204. More precisely, the drive unit 262 drives a shaft 270 which, for instance via a schematically illustrated ball screw mechanism 272 forces the piston 202 to reciprocate. The ball screw mechanism 272 comprises a nut 274 which is rotated by the shaft 270, for instance via engaging tooth wheels 276. The rotating nut 274 cooperates with a mandrel as a piston actuator 278 so as to drive the piston actuator 278 along the horizontal direction according to FIG. 2, forwardly and backwardly. The piston actuator 278 then moves the piston 202 via a contact area 280, The ball screw mechanism 272 thereby transforms a rotational motion of the drive unit 262 into a linear motion of the piston 202.

Coming now to the pump head 250, it comprises the piston chamber 204 defining or delimiting a working volume 208 in which the piston 202 reciprocates. A piston member 200 which comprises the piston 202 is mounted in the working volume 208 of the piston chamber 204 to thereby displace fluid in the piston chamber 204. The fluid is supplied via a fluid inlet interface 264 and leaves the working volume 208 of the piston chamber 204 via a fluid outlet interface 266.

The piston member 200 comprises the high-pressure compatible piston 202 and a sealing 206 which together constitute one common integral member. Consequently, piston 202 and sealing 206 reciprocate together within the working volume 208 of the piston chamber 204. As can be taken from FIG. 2, the sealing 206 is attached to a front end of the piston 202 and is connected here in a purely mechanical manner, i.e. by a form closure connection supported by friction only and without adhesive. The sealing 206 forms the front end of the piston member 200 and thereby contributes to the displacement of the fluid in the working chamber 208. In the shown embodiment, the material of the sealing 206 is a soft resilient plastic material being chemically inert against chromatographic solvents such as methanol and acetonitrile. The piston 202, in turn, is made of a ceramic material and is robust and stiff. When the piston member 200 is in its front end position, i.e. close to a flange face 290 of the working chamber 208, its distance from the flange face 290 may be as small as for instance only 0.5 mm. This results in an extremely small dead volume.

Figure 3:
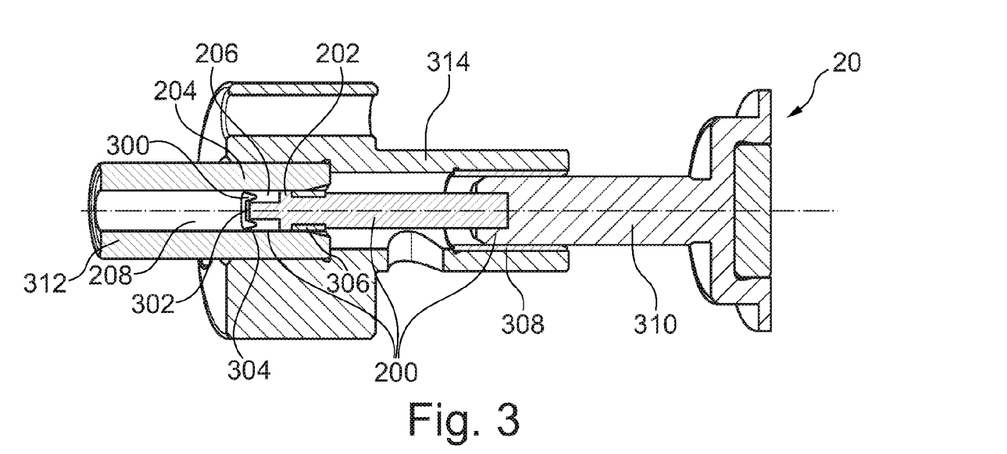
FIG. 3 illustrates a schematic view of a core of a pump according to an exemplary embodiment of the invention for a sample separation apparatus.

FIG. 3 shows a cross-sectional view of part of a pump 20 according to another exemplary embodiment of the invention. In the embodiment of FIG. 3, details of the sealing 206 according to an exemplary embodiment can be seen. The sealing 206 of FIG. 3 has at its front end an annular recess 300 delimiting a central protrusion 302 with regard to an exterior annular sealing lip 304. The sealing lip 304 seals between the piston chamber 204 and the piston member 200. The central protrusion 302 reduces the dead volume and contributes to the displacement of fluid. In the annular recess 300, a biasing element such as a spring, which improves the sealing performance, can be accommodated (see FIG. 6).

FIG. 3 shows that the piston 202 is mounted in a piston base 310 which may actually cooperate with piston actuator 278 (not shown in FIG. 3). The piston chamber 204 is here constituted by a hollow cylinder 312 (which may be made of a ceramic material) and a surrounding base body 314.

Furthermore, the pump 20 of FIG. 3 has a sleeve-shaped rear piston guide 308 mounted statically on the base body 314 and a separate sleeve-shaped front piston guide 306 mounted on the piston 202 behind the sealing 206 further improving the accuracy of the guidance of the piston member 200 in the working chamber 208. This reduces the danger of an undesired abutment of the piston 200 at the piston chamber 204.

Figure 4:
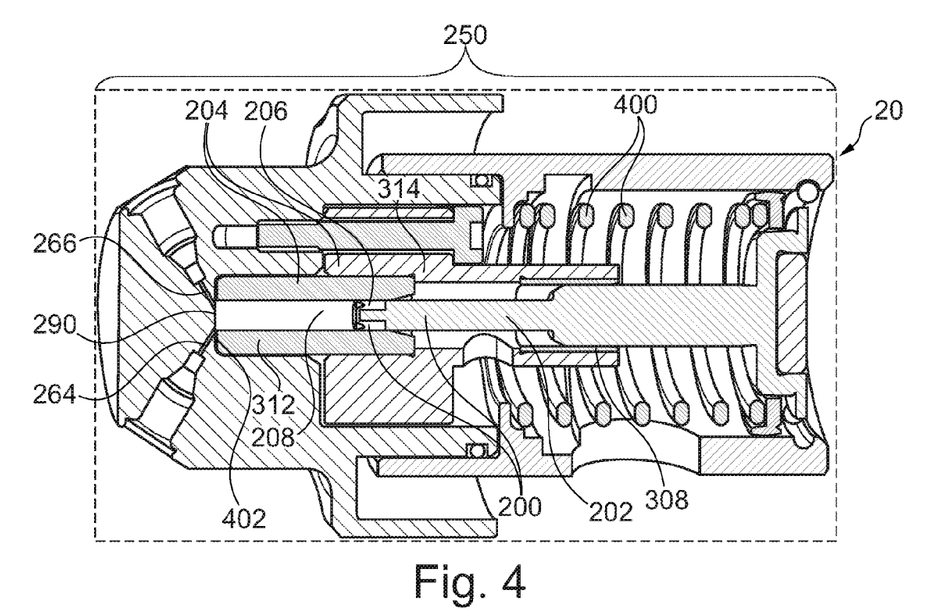
FIG. 4 illustrates a schematic view of a pump according to an exemplary embodiment of the invention embodied as metering pump for a sample injector of a sample separation apparatus.

FIG. 4 shows a cross-sectional view of a pump 20 according to yet another exemplary embodiment of the invention embodied as metering pump for a sample injector 40 of a sample separation apparatus 10. FIG. 4 shows a biasing element 400 embodied as a helical spring which can be biased when the piston member 200 moves forwardly. This biases the biasing element 400 so that a later relaxation of the biasing element 400 contributes to the back-driving of the piston member 200 to its position on the right-hand side of FIG. 4. Pump 20 comprises a gold-plated flat sealing 402 at the flange face sealing between the hollow cylinder 312 and the base body 314.

Figure 5:
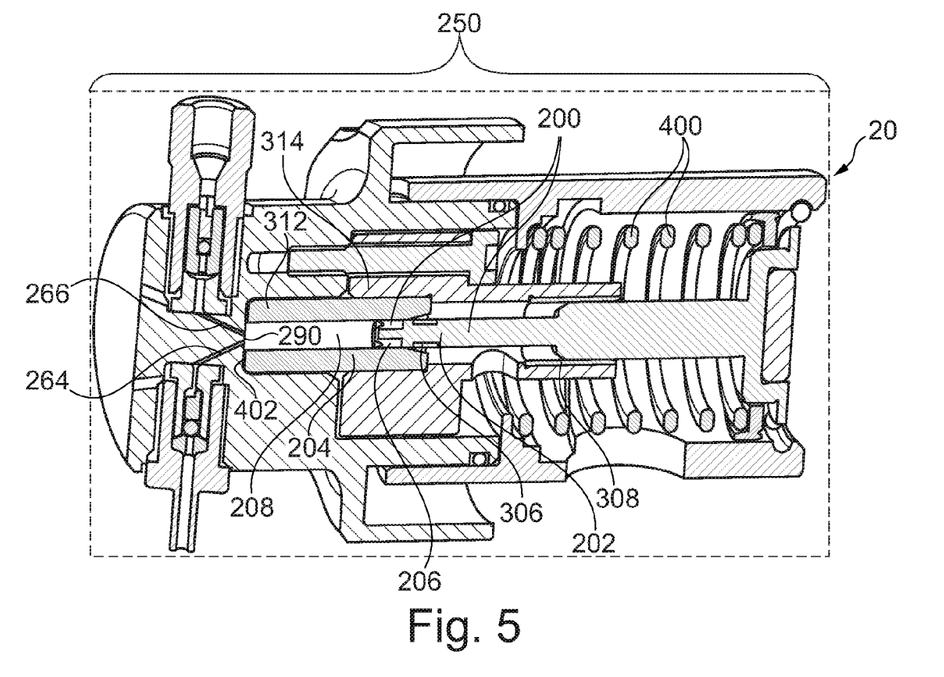
FIG. 5 illustrates a schematic view of a pump according to an exemplary embodiment of the invention embodied as mobile phase pump for pumping mobile phase under high pressure in a sample separation apparatus.

FIG. 5 shows a pump 20 according to yet another exemplary embodiment of the invention which has another arrangement of fluid inlet interface 264 and fluid outlet interface 266. The pump 20 is embodied as mobile phase pump for pumping mobile phase under high pressure in a sample separation apparatus 10.

Figure 6:
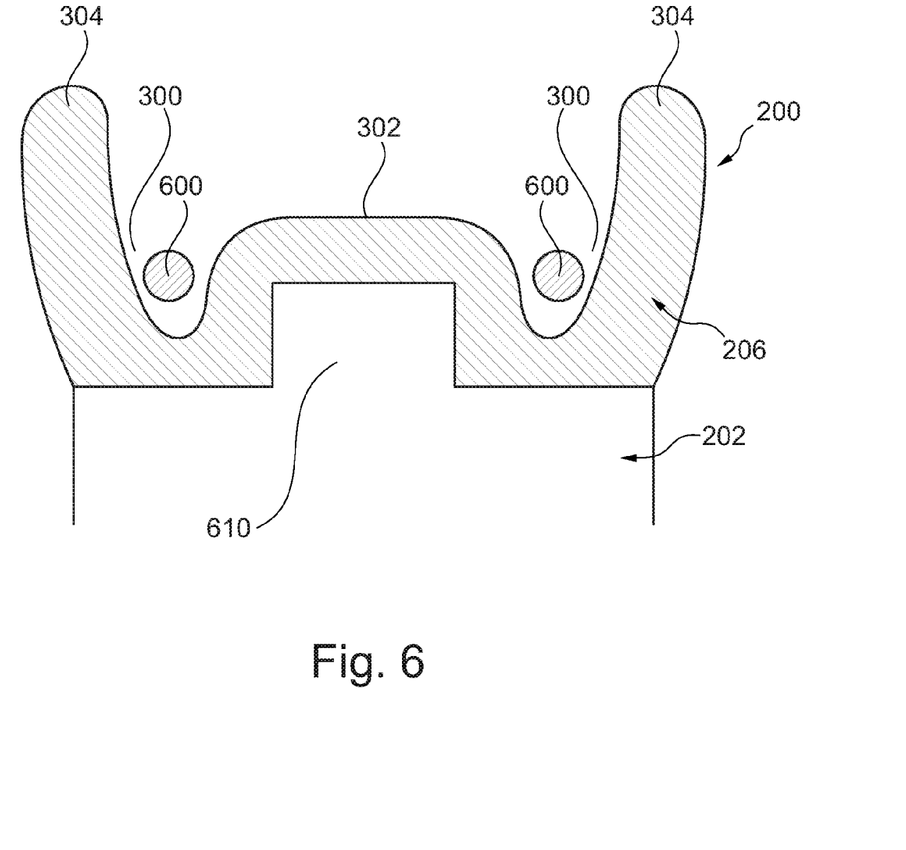
FIG. 6 illustrates a cross-sectional view of a piston member according to an exemplary embodiment of the invention.

FIG. 6 shows a cross-sectional view of a front portion of a piston member 200 similar to the embodiments of FIG. 3 to FIG. 5 and illustrates details of its sealing 206. The sealing 206 is attached in a purely mechanical manner onto a protrusion 610 at a front end of the piston 202. Thus, a form closure can form the connection between piston 202 and sealing 206. Furthermore, a circular spring as biasing member 600 is accommodated within the annular groove 300 formed between the central protrusion 302 and the exterior sealing lip 304 of the sealing 206.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A high-pressure pump configured for pumping fluid in an HPLC sample separation apparatus, the pump comprising:
  a piston chamber;
  a piston member configured for reciprocating in a reciprocation direction in the piston chamber for displacing fluid;
  a sealing for sealing between the piston member and the piston chamber, wherein the sealing is mounted on the piston member so as to reciprocate together with the piston member;
  a base body at least partly surrounding the piston chamber; and
  a static piston guide unit disposed along an interior wall of the base body and configured for guiding the piston member along the reciprocation direction.

2. The pump of claim 1, further comprising:
  a pump head which comprises the piston member; and
  a pump base to be assembled with the pump head and comprising a piston drive configured for driving the piston member to reciprocate within the piston chamber in an assembled state.

3. The pump of claim 2, further comprising a back-driving mechanism arranged to provide a back-driving force to the piston member after the piston drive has forwarded the piston member to its front end position in the piston chamber to move the piston member in the reciprocation direction.

4. The pump of claim 1, wherein the pump is configured as one of:
  a metering device for a sample injector of the sample separation apparatus for metering a fluidic sample to be separated into fractions;
  a mobile phase drive for driving a mobile phase towards a separation unit of the sample separation apparatus.

5. The pump of claim 1, wherein the pump comprises at least one of:
  a fluid inlet interface configured for providing a fluid communication between fluid to be pumped and a working volume of the piston chamber;
  a fluid outlet interface configured for providing a fluid communication with the working chamber for outletting fluid pumped by the pump.

6. The pump of claim 1, wherein the sealing is arranged at a front end of the piston member.

7. The pump of claim 6, wherein the sealing is arranged at the front end of the piston member so as to constitute an entire flange face of the piston member.

8. The pump of claim 1, wherein the sealing comprises a front face, a central protrusion, an exterior sealing lip, and at an annular recess at the front face separating the central protrusion from the exterior sealing lip.

9. The pump of claim 1, further comprising a biasing member arranged at the sealing for promoting the sealing performance by a biasing force.

10. The pump of claim 9, wherein the sealing comprises an annular recess, and the biasing member is arranged within the annular recess.

11. The pump of claim 1, wherein the sealing is fastened at the piston member by a purely mechanical connection.

12. The pump of claim 1, wherein:
  the static piston guide unit comprises a sleeve disposed along an interior wall of the base body and upon which the piston member slides along.

13. The pump of claim 1, wherein the piston member is mounted in the piston chamber so that the piston member is forwardable up to a front end position of the piston member in the piston chamber, and the front end position is located less than 0.5 mm from a flange face of the piston chamber delimiting a working volume of the piston chamber.

14. The pump of claim 13, wherein the front end position is located less than 0.3 mm from the flange face.

15. The pump of claim 1, comprising a movable piston guide unit arranged on the piston member.

16. The pump of claim 1, wherein the piston chamber is composed of a ceramic material.

17. A sample separation apparatus for separating a fluidic sample in a mobile phase into a plurality of fractions, the apparatus comprising:
  the high-pressure pump of claim 1 configured for driving a fluid comprising at least one of the mobile phase and the fluidic sample; and
  a separation unit configured for separating the fluidic sample into the plurality of fractions.

18. The sample separation apparatus of claim 17, wherein the pump is configured as one of:
  a mobile phase drive configured for driving the mobile phase towards the separation unit;
  a metering device of a sample injector of the sample separation apparatus for metering the fluidic sample to be injected into the mobile phase and subsequently in the separation unit.

19. The sample separation apparatus of claim 17, further comprising at least one of the following features:

a sample injector configured for injecting the fluidic
sample into the mobile phase;
a detector configured to detect separated fractions of the
fluidic sample;
a fractioner unit configured to collect separated fractions
of the fluidic sample;
a data processing unit configured to process data received
from the sample separation apparatus;
a degassing apparatus for degassing the mobile phase;
the sample separation apparatus is configured as a chromatography device.

* * * * *